United States Patent
Koshti et al.

(10) Patent No.: US 9,187,407 B2
(45) Date of Patent: Nov. 17, 2015

(54) METHOD TO PRODUCE N-ACYL AMINO ACID SURFACTANTS USING N-ACYL AMINO ACID SURFACTANTS OR THE CORRESPONDING ANHYDRIDES AS CATALYSTS

(71) Applicant: GALAXY SURFACTANTS LTD., Navi Mumbai (IN)

(72) Inventors: Nirmal Koshti, Upper Saddle River, NJ (US); Bharat Bhikaji Parab, Mumbai (IN); Rajendra Subhash Powale, Old-Panvel (IN); Archana Kishor Desai, Mumbai (IN); Kamlesh Keshwar Barai, Mumbai (IN); Pradnya Mandar Katdare, Ambarnath (IN); Bhagyesh Jagannath Sawant, Kalyan (IN); Santosh Vishnu Kadam, Mumbai (IN); Srinivas Uppalaswamy Pilli, Mumbai (IN)

(73) Assignee: GALAXY SURFACTANTS LTD., Pawne, Navi Mumbai, Maharashtra (IN)

( * ) Notice: Subject to any disclaimer, the term of this patent is extended or adjusted under 35 U.S.C. 154(b) by 0 days.

(21) Appl. No.: 14/409,540

(22) PCT Filed: Sep. 28, 2012

(86) PCT No.: PCT/IB2012/055197
§ 371 (c)(1),
(2) Date: Dec. 19, 2014

(87) PCT Pub. No.: WO2014/030038
PCT Pub. Date: Feb. 27, 2014

(65) Prior Publication Data
US 2015/0141682 A1    May 21, 2015

(30) Foreign Application Priority Data

Aug. 23, 2012 (IN) .......................... 2453/MUM/2012

(51) Int. Cl.
| C07C 231/02 | (2006.01) |
| C07C 303/22 | (2006.01) |
| C07C 303/26 | (2006.01) |
| C07C 51/60 | (2006.01) |

(52) U.S. Cl.
CPC .............. *C07C 231/02* (2013.01); *C07C 51/60* (2013.01); *C07C 303/22* (2013.01); *C07C 303/26* (2013.01)

(58) Field of Classification Search
None
See application file for complete search history.

(56) References Cited

U.S. PATENT DOCUMENTS

| 6,770,783 B1 | 8/2004 | Busch et al. |
| 2005/0085651 A1 | 4/2005 | Kitamura et al. |
| 2010/0273879 A1* | 10/2010 | Klug et al. .................... 514/554 |

FOREIGN PATENT DOCUMENTS

| DE | 2656126 A1 | 7/1977 | |
| FR | 2337121 B1 * | 7/1978 | ............. C07C 51/60 |
| WO | 2009065530 A2 | 5/2009 | |

OTHER PUBLICATIONS

FR 2337121 (B1), Poudres & Explosifs STE Nale, Acid chloride production by phosgenation of carboxylic acid—using carboxylic acid diamide as catalyst to facilitate separation of product, 1978, English translation, pp. 1-7. (relates to DE2656126 (A1).*
Mhaskar, S.Y., et al., Syntesis of N-acyl amino acids and correlation of structure with sufactant properties of their sodium salts, 1990, JAOCS, vol. 67, No. 12, pp. 1015-1019.*
Ralston, A.W., et al., Actin of Sotium upno high molecular wtight fatty acid chlorides, 1939, Journal of the American Chemical Society, vol. 61, pp. 1019-1020.*
Notification of Transmittal of the International Preliminary Report on Patentability for PCT/IB2012/055197 mailed Jul. 3, 2014 (15 pages).

* cited by examiner

*Primary Examiner* — Yate K Cutliff
(74) *Attorney, Agent, or Firm* — Vincent J. Allen; Shaukat A. Karjeker; Carstens & Cahoon, LLP

(57) ABSTRACT

A process of producing N-acyl amino acid based surfactants of Formula I,

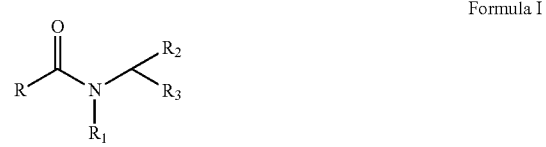

Formula I wherein, R is selected from C6 to C22 alkyl group, $R_1$ is selected from H, C1 to C4 alkyl, $R_2$ is selected from all groups on α carbon of natural amino acids, $R_3$ is selected from COOX, $CH_2-SO_3X$, X is selected from $Li^+$, $Na^+$ or $K^+$. The process comprising steps of:
A) preparing fatty acid chlorides by halogenating fatty acids with either phosgene or thionyl chloride in the presence of catalytic amount of same or other N-acyl amino acid surfactant of Formula I or anhydrides of same surfactant; and
B) reacting fatty acid chloride of step (A) with an amino acid in the presence of a base.

9 Claims, No Drawings

METHOD TO PRODUCE N-ACYL AMINO ACID SURFACTANTS USING N-ACYL AMINO ACID SURFACTANTS OR THE CORRESPONDING ANHYDRIDES AS CATALYSTS

FIELD OF INVENTION

The present invention relates to a cost-effective two-step process for the manufacture of amino acid based surfactants using same surfactants as catalysts for synthesizing the intermediate of high quality and with quantitative yield. More particularly, the present invention relates to a process for the preparation of N-acyl amino acid surfactants by catalyzing the synthesis of fatty acid chloride by the same N-acyl amino acid surfactants that are being manufactured.

BACKGROUND AND PRIOR ART OF THE INVENTION

N-Acyl amino acid surfactants are widely used in personal care applications in addition to the other industrial applications. They fall in the category of anionic surfactants and are significantly milder than the rest of the anionic surfactants. For example, surfactants like sodium lauroyl sarcosinate, sodium myristoyl sarcosinate, sodium cocoyl glycinate, sodium cocoyl N-methyl taurate are commercially used in face washes, body washes since they exhibit good cleansing power and are milder to skin and hair compared to other anionic surfactants. Alkanoyl sarcosinates find applications in mouth washes and in dentifrices, in general, due to their bacteriostatic activity. There are a host of other areas where N-acylated amino acids are commercially used such as in petroleum products, as lubricants, in metal processing and ore floatation. (N-acylated amino acid as surfactants, J. D. Spivack, Chapter 16, in 'Anionic surfactants, Vol 7, Surfactant Science Series, Edited by W. M. Linfield). Commercially, they are manufactured from a two-step synthesis that involves fatty acid and various amino acids such as glycine, sarcosine, N-methyl taurine, alanine, aspartic acid, glutamic acid, glutamine and arginine. These are some of the most commonly used amino acids that are used to manufacture N-acyl amino acid surfactants. However, virtually all amino acids, chiral or racemic, natural or synthetic can be used in the manufacture of N-acyl amino acid surfactants. Also, amino acids used in the surfactant manufacture do not have to be α-amino acids. Also, the acid group in these amino acids can be any other acidic group other than the carboxylic group. Amino sulphonic acids (e.g. N-methyl taurine) have been condensed with fatty acid chlorides and to create commercial surfactants such as sodium N-methyl-N-cocoyl taurate. In the manufacture N-acyl amino acid surfactants fatty acid or a mixture of fatty acids is reacted with amino functionality of amino acids through the intermediacy of fatty acid chloride under typical Schotten Baumann conditions as shown in scheme 1 (U.S. Pat. No. 2,790,7799 (1953), U.S. Pat. No. 2,790,779 (1957), U.S. Pat. No. 3,945,931 (1974)).

scheme 1

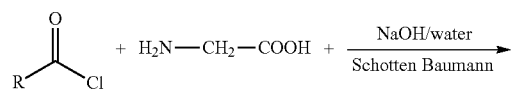

-continued

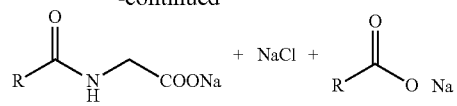

Schotten Baumann condensation between fatty acid chloride and an amino acid is typically done in aqueous medium, however, use of mixed solvent systems (solvent and water) is also reported (U.S. Pat. No. 6,703,517 (2002), U.S. Pat. No. 6,569,829 (1999), US Appl. Pub. No 2005/0085651 (2004) and WO2009/065590 (2009)). A few other patents teach about preparation and purification of N-acyl amino acid surfactants that are essentially made by following the same route of condensing fatty acid chloride with amino acids (JP Pat No 2923101 (1991), JP Appl Pub No 04-149163 (1990), JP Pat No 3362468 (1993)).

scheme 2

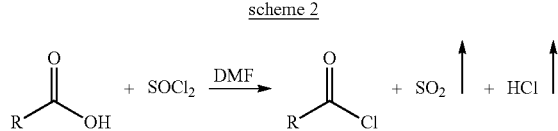

scheme 3

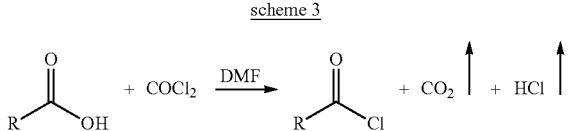

The precursors of N-acyl amino acid surfactants, the fatty acid chlorides, industrially, are manufactured by reacting fatty acids and a halogenating agent, either phosgene or thionyl chloride as depicted in schemes 2 and 3. The chlorination is usually catalyzed by N, N-dimethyl formamide (DMF). DMF or similar substituted formamides form a complex (Vilsmeier complex) with $COCl_2$ or $SOCl_2$ which is the actual catalytic species (U.S. Pat. No. 5,430,186; U.S. Pat. No. 5,623,082; U.S. Pat. No. 5,200,560; U.S. Pat. No. 5,278,328 & U.S. Pat. No. 5,166,427) in chlorination of acids.

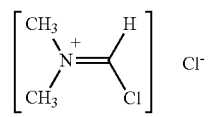

Vilsmeier Complex

At the end of the reaction isolating the fatty acid chloride (product) from the catalyst complex has always been a difficult problem to overcome. Several attempts have been made but clean separation of the catalyst complex from the product acid chloride is generally not possible. (U.S. Pat. No. 5,166,427 (1992), U.S. Pat. No. 5,200,560 (1993), U.S. Pat. No. 6,770,783 (2004) U.S. Pat. No. 6,727,384 (2004) and U.S. Pat. No. 5,247,105 (1993).

The serious disadvantages and complications arising out of the presence of this dark colored catalyst complex (Vilsmeier complex) in the product are well-documented and the most attempts have been made towards improving 'phase-separation' that is separating the catalyst complex phase from the product phase.

Thus, removal of DMF or similar catalytic substances, by either phase separation, or fractionation/distillation entails additional processing and loss of yield of valuable product. A major portion of the Vilsmeier compounds so formed are separated out on the completion of the reaction by allowing phases to separate. The corboxamide-chlorinating agent complex tends to settle as a black/brown tar at the bottom of the reactor vessel. Phase separation is the most attempted method for purifying acid chlorides as disclosed in U.S. Pat. No. 5,166,427 (1992), U.S. Pat. No. 5,200,560 (1993), U.S. Pat. No. 6,770,783 (2004), and U.S. Pat. No. 6,727,384 (2004) and U.S. Pat. No. 5,247,105 (1993).

Distillation (fractionation) is another way to isolate the product but not all acid chlorides are amenable to distillation. The catalyst complex (Vilsmeier complex) exists in ionic form and hence is not easy to get rid of the same by distillation/fractionation of acid chloride. The complex keeps decomposing while distilling. Secondly, the losses of distillation/fractionation (fractions with formamide catalyst and residue left after the distillation) are unavoidable.

Another serious concern is the toxicity of these formamides or any other organic molecules similar to DMF. DMF is listed in hazardous substances and is reported have chronic toxic effect and health hazard rating of 2. Also, no toxicity data are available for the other formamides, the analogues of DMF that are capable of being catalysts but are expected to exhibit similar or higher toxicity. In addition to the concern of health hazard associated with formamides, the analogs of DMF do suffer from the same difficulty of isolating fatty acid chloride (product) from the reaction mass when used as catalysts since they do form Vilsmeier complexes with halogenating agents. Hence the fatty acid chlorides made by halogenating fatty acids either with phosgene or thionyl chloride using formamides, acetamides, or any other analogues as catalysts, need additional steps of purifications such as distillation, phase separation or crystallization etc. (DE 2656126 (1977)). These additional steps result in significant loss of yield, higher energy consumption and longer batch cycle time resulting into lower productivity.

Since the making of the key intermediates, the fatty acid chlorides, by the current processes of the existing art, is cumbersome and inefficient, it impacts the quality and the cost of all downstream products such as the N-acyl amino acid surfactants with world consumption of is estimated to be 250,000 metric tonnes.

Hence there is a need to significantly improve the manufacturing process that can reduce the losses due to distillation and avoid any other purification step of the intermediate, and reduce batch cycle time giving higher productivity.

The present invention relates to the manufacture of amino acid based surfactants using same surfactants as catalysts for synthesizing the intermediate of high quality and with quantitative yield. The overall process is 'green' (significantly reduced batch time, low energy consumption, without any wastage and effluent generation (no residue after distillation/ fractionation), and extremely cost-effective (low energy consumption), efficient (faster rate of catalysis). Moreover, this process described in the present application avoids use of toxic catalysts and is applicable to entire class of N-acyl amino acid surfactant family.

OBJECTS OF THE INVENTION

It is an object of the present invention to overcome the drawbacks of the prior art.

It is another object of the present invention to provide a process for the manufacture of amino acid based surfactants using same surfactants as catalysts for synthesizing the intermediate of high quality and with quantitative yield.

It is yet another object of the present invention to provide a cost-effective two-step process for the industrial manufacture of the entire class of N-acyl amino acid surfactants.

SUMMARY OF THE INVENTION

The present invention relates to a process of producing N-acyl amino acid based surfactants of Formula I,

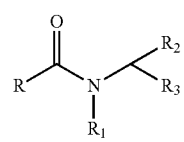

Formula I wherein, R is selected from C6 to C22 alkyl group, $R_1$ is selected from H, C1 to C4 alkyl, $R_2$ is selected from all groups on a carbon of natural amino acids, $R_3$ is selected from COOX, $CH_2$—$SO_3X$, X is selected from $Li^+$, $Na^+$ or $K^+$;

said process comprising steps of

A) preparing fatty acid chlorides by halogenating fatty acids with either phosgene or thionyl chloride in the presence of catalytic amount of same or other N-acyl amino acid surfactant of Formula I or anhydrides of same surfactant, Formula II,

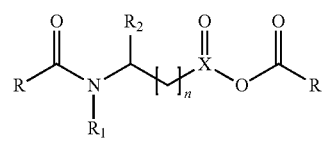

Formula II wherein, R=C6 to C22 alkyl group, $R_1$=H, C1 to C4 alkyl, $R_2$=all groups on α carbon of natural amino acids, n=0 to 4, X=C, SO and B) reacting fatty acid chloride of step (A) with an amino acid in the presence of a base under typical aqueous Schotten Baumann conditions such that said process does not employ a step of purification.

DETAILED DESCRIPTION OF THE INVENTION

The present invention relates to a cost-effective process for the manufacture of amino acid based surfactants using same surfactants as catalysts for synthesizing the intermediate of high quality and with quantitative yield.

The method of this invention teaches the manufacture of N-acyl amino acid surfactants of Formula I

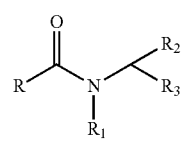

Formula I wherein, R represents alkyl chain with carbon atoms ranging from 6 to 22, $R_1$ represents H, or small alkyl chains ranging from C1 to C4, $R_2$ represents all groups on a carbon of natural amino acids, $R_3$ represents an acidic group such as carboxyl or sulphonyl with a counter cation of alkali metals as in COOX, $CH_2$—$SO_3X$, where X=$Li^+$, $Na^+$ or $K^+$.

The process of the present application involves two steps. The first step is the manufacture of fatty acid chloride and in the second step the fatty acid chloride manufactured in the first step is reacted with an amino acid in aqueous or mixed water-solvent medium in the presence of base to obtain the N-acyl amino acid surfactants.

The alkyl chain represented by R can be even numbered or odd numbered, linear or branched chains. It can be a single chain or a mix of several alkyl chains ranging from C 6 to C 22. The alkyl chain can be completely saturated or it can be unsaturated with one or more double bonds. Since these alkyl chain are derived from fatty acids that occur in nature, mostly, in the form of animal fats or vegetable oil. Unsaturated alkyl chains can be derived from oleic acid, recinoleic acid, linolic acid, linolenic acid, elaeosteric acid, eicosenoic acid, euricic acid, docosodienoic acid and undecylenic acid. The saturated fatty acids are usually derived from palm/palm kernel oil or coconut oil and are all even numbered ranging from octanoic acid (C8) to stearic acid (C18). Fatty acids with higher number of carbons (C18 to C22) are derived from mustard oil, tung oil and rapeseed oil.

The saturated/unsaturated fatty acids are converted to the corresponding acid chlorides by either treating them with thionyl chloride or phosgene. Both reactants are reacted with each other in stoichiometric equivalent quantity or up to 3% excess of chlorinating agent (mole ratio, fatty acid:chlorinating agent:1:1.03). The halogenations of fatty acids with either phosgene or thionyl chloride are done at 20 to 45° C. under nitrogen blanket with a scrubbing system for absorption of by-products HCl and $SO_2$. On plant scale, the well established 'closed loop' technique can be followed where $SO_2$ and HCl are separated and are conveniently used whereby $SO_2$ is converted back to $SOCl_2$.

According to the present invention the types of amino acids that are used in the synthesis of compounds of Formula I are naturally occurring α-amino acids (Glycine, Alanine, Valine, Leucine, Isoleucine, Methionine, Proline, Cystein, Phenyl alanine, Tyrosine, Tryptophan, Arginine, Lysine, Histidine, Aspartic acid, Glutamic acid, Serine, Threonine, Aspergine, Glutamine), unnatural amino acids (opposite 'D' stereochemistry), mixtures of stereoisomers, unnatural amino acids (amino propionic acid, N-methyl taurine, Sarcosine). In short, the amino acids required for the synthesis of compounds of Formula I need to have one primary or secondary amino group at one end and an acid group, either carboxylic or sulphonic at the other end.

While synthesizing the N-acyl amino acid surfactants, fatty acid chloride is added to a cooled (10 to 15° C.) and stirred aqueous solution of amino acid in its salt form with alkali metals. The cations of salt form of the amino acids are alkali metal ions like potassium, sodium or lithium. For this condensation (Schotten Baumann reaction) the ratio of fatty acid chloride to amino acid varies from 1:1 to 1:1.03. To a stirred and cooled solution of amino acid, one equivalence of base (in solution form) and one equivalence of fatty acid chloride are added simultaneously maintaining the stoichiometric ratio and the pH of the reaction mass between 10 to 11, preferably between 10.3 to 10.6. The Schotten-Baumann reaction is a rapid reaction and results in very clean product with stoichiometric generation of byproduct, the salt, alkali metal chloride, depending on the base employed. Small extent of hydrolysis of fatty acid chloride does result in generation of corresponding alkali metal salts of fatty acids. The N-acyl products that are obtained are practically colorless and odorless. The products obtained are free of any contamination due to the residual catalyst since the catalyst used is the same surfactant that is being manufactured.

The present application teaches the use of N-acyl amino acid catalysts for the manufacture of fatty acid chloride that would give the same surfactant after performing the second step of Schotten Baumann reaction. The fatty acid chloride step employs 0.05 to 2 mole % of N-acyl amino acid surfactants as catalysts. For example, in Example no. 4 of experimental section, synthesis of sodium cocoyl glycinate is accomplished using cocoyl chloride that was made from reaction of coco fatty acid and thionyl chloride catalyzed by sodium cocoyl glycinate itself. Similarly, Example No. 6 describes, synthesis of sodium lauroyl glycinate from lauroyl chloride and glycine in the presence of base. The lauroyl chloride for this conversion was synthesized from lauric acid and thionyl chloride under the catalytic influence of sodium lauroyl glycinate.

The N-acyl amino acid surfactants indeed catalyze the halogenations reactions of fatty acids and generally work very efficiently at 0.02 to 2.00 mole % concentration level. It is quite possible that the N-acyl amino acid surfactant in its salt form, for example, sodium lauroyl glycinate, (Formula III, R=C11 and $R_2$=H) reacts with halogenating agent giving the Vilsmeier complex that catalyzes the fatty acid chloride formation and once the fatty acid chloride (lauroyl chloride) is formed then it can react with sodium salt of lauroyl glycinate to form the anhydride, N-lauroyl glycenic lauric anhydride (Formula IV, R=C11, $R_2$=H as shown in scheme 4. So Catalyst I, Formula IV, R=C11, $R_2$=H) is produced in situ that can complex with the halogenating agent and forming the reactive Vilsmeier type active catalytic species that has phenomenal solubility in fatty reactants due the presence of two long alkyl chains on the both sides of anhydride moiety. This high degree of liposolubility helps in achieving perfect conditions for homogeneous catalysis. This hypothesis was quickly tested by synthesizing the anhydride, catalyst I (Formula IV, R=C11, $R_2$=H) and using it as a catalyst in halogenating lauric acid.

Stoichiometric quantities of sodium lauroyl glycinate (Formula III, R=C11, $R_2$=H) and lauroyl chloride were stirred in dichloromethane at room temperature for 12 h. Filtration of the salt yielded the desired N-lauroyl glycenic lauric anhydride as a waxy solid (scheme 4, Formula IV, R=C11, $R_2$=H). Infrared spectrum N-lauroyl glycenic lauric anhydride showed the characteristic stretching frequency for the anhydride linkage at 1750 and 1817 $cm^{-1}$. The NH stretch and carbonyl stretch appeared at 3294 $cm^{-1}$ and at 1643 $cm^{-1}$ respectively.

Proton magnetic resonance spectrum of the same molecule in deuteriated chloroform showed the signal for methylene protons of glycine moiety at δ 2.46.

This anhydride, catalyst I (Formula IV, R=C11, $R_2$=H) thus obtained, was then employed as catalyst for the synthesis of lauroyl chloride at 0.13 mole % level (scheme no 5, Example 1). The lauroyl chloride obtained was practically colorless with very good conversion (Table 1 in Experiment 1). This lauroyl chloride was then used without any purification and was reacted with stoichiometric quantity of glycine in water at 10 to 15° C. in the presence of equivalent quantity of base (Experiment 1). The residual catalyst I (Formula IV, R=C11, $R_2$=H) present in the lauroyl chloride can undergo nuclophilic attack by glycine in the next step of Schotten Baumann reaction to afford two molecules of sodium lauroyl glycinates. The competing nucleophile water (alkaline pH) can hydrolyze the anhydride to yield sodium lauroyl glycinate and sodium laurate. The final product that is aqueous solution of sodium lauroyl glycinate with 30% solids content will have 0.0002 mole % of sod laurate generated by hydrolysis of the anhydride catalyst is. In the presence of a better nucleophile in the form of glycine it seems highly unlikely that the residual catalyst (Formula IV, R=C11, $R_2$=H) in lauroyl chloride would undergo alkaline hydrolysis exclusively.

Scheme 4

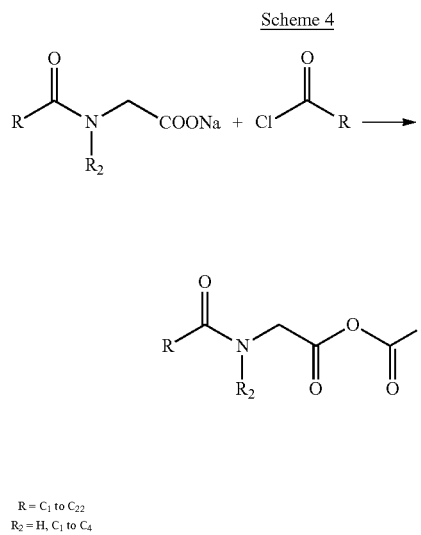

R = $C_1$ to $C_{22}$
$R_2$ = H, $C_1$ to $C_4$

Scheme 5

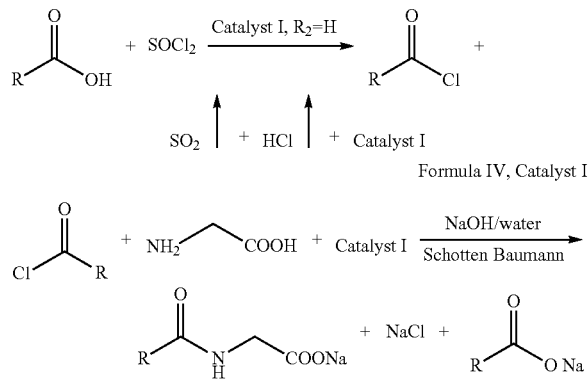

The rate of catalysis of lauroyl chloride formation from lauric acid and thionyl chloride either by sodium lauroyl glycinate (Formula III, R=C11, $R_2$=H) or N-lauroyl glycenic lauric anhydride (Formula IV, R=C11, $R_2$=H) was found to be the same qualitatively at same mole %.

Also, sodium lauroyl glycinate, the N-acyl amino acid surfactant, prepared from the above lauroyl chloride obtained by using either sodium lauroyl glycinate (Formula III, R=C11, $R_2$=H) as a catalyst or N-lauroyl glycenic lauric anhydride (Formula III, R=C12, $R_2$=H) as a catalyst, offered the surfactant of the same quality.

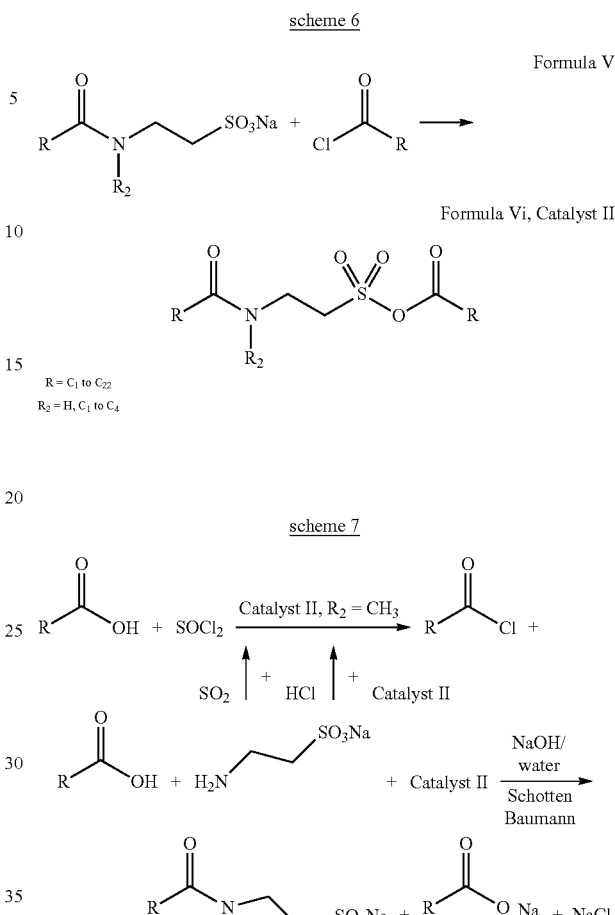

The catalysis of chlorination of fatty acid was confirmed with other N-acyl amino acid surfactants like sodium lauroyl N-methyl taurate (Experiment No 7) (Formula IV, R=C12, $R_2$=$CH_3$ scheme 6) and using taurinic lauric anhydride (Experiment No 2, Formula VI, R=C11, $R_2$=$CH_3$ scheme 7). The lauroyl chloride with residual catalyst (mixed anhydride of Formula V) thus obtained was converted to sodium lauroyl, N-methyl taurate by reacting it with sodium N-methyl taurate under aqueous Schotten Baumann conditions.

According to the present invention any N-acyl amino acid surfactant essentially can catalyze chlorination of any fatty acid or mixture of fatty acids to yield corresponding fatty acid chlorides at 0.02 to 2.0 mole % concentration level. Example 8 shows a facile synthesis of sodium cocoyl glycinate wherein the synthesis of cocoyl chloride is accomplished by catalyzing reaction between coco fatty acid and thionyl chloride by sodium N-lauroyl, N-methyl taurate.

It is apparent to those with common knowledge of the art that the fatty acid chlorides thus produced are not only suitable for a batch process of Schotten Baumann reaction but also for a continuous process for manufacturing N-acyl amino acid surfactants by reacting fatty acid chlorides, amino acid salts and the bases.

According to the invention, the process described is very cost-effective since it avoids purification steps that result in significant reduction in energy consumption. The process of the present invention also avoids laborious steps of purifications and loss of product that entails the purification steps.

According to another embodiment of the invention the process avoids all the toxic catalysts used in the prior art. The two-step process is absolutely 'green' since it does not generate any effluent (no waste disposal), consumes less power, involves fewer unit operations, affords quantitative yields and above all, uses a biodegradable, eco-friendly catalyst. In summary, the present patent application discloses a self-catalyzed N-acyl amino acid surfactant synthesis.

The above described features, benefits and advantages of the present disclosures will be appreciated and understood by those skilled in the art from the following detailed description and the claims.

Advantages of the Invention

1) Use of same N-acyl amino acid surfactants to catalyze the key step (the precursor) in the manufacture of N-acyl amino acid surfactants.
2) The catalyst for the intermediate acid chloride is the same surfactant that is being manufactured and hence the intermediate fatty acid chloride does not have to be purified by additional steps (distillation/crystallization) that often lead to the substantial loss of yield and increased batch cycle time and increased energy consumption.
3) Unlike the processes of the prior art, the current process of the present invention uses completely degradable catalyst for the manufacture of the intermediate acid chlorides.
4) The N-acyl surfactant catalysts work equally well with both industrial halogenating agents. These catalyst work very well with phosgene and thionyl chloride while creating fatty acid chloride The by-product of phosgenation is $CO_2$ whereas with thionyl chloride the by-product is $SO_2$ that can be converted into surfuryl chloride and subsequently thionyl chloride by a well established 'closed loop' chemistry (U.S. Pat. No. 5,489,400).
5) Since the distillation/crystallization/phase separation steps are obviated during the manufacture of fatty acid chloride, there is no generation of effluent and hence in addition to the advantage of lesser energy consumption, a significant saving on the waste disposal is accomplished. Thus, the process of making N-acyl surfactants of this patent application is completely 'green' and nothing is let out in the environment.
6) Unlike the processes of the prior art the process of the current patent application does not use any toxic catalysts and hence the issue of product isolation from the toxic catalyst does not arise.
7) The process of this patent application is uses biodegradable and non toxic catalysts. It involves lesser chemical engineering unit operations and offers high throughput with quantitative conversions and yield. This makes the process cost-effective as well as eco-friendly and sustainable.

EXAMPLES

The present invention is now described by way of working on limiting illustrative examples. The following examples are given in illustration in more details but the invention is not limited to the examples.

Fatty acids were procured from Natural Oleo-chemicals, Malaysia whereas thionyl chloride from Transpek Industries, Vadodara, India. Phosgene trimer, glycine and sodium N-methyl taurate were procured from Aldrich.

The color value is used as an indication of the purity of the acid chloride product. The color value of intermediates and N-acyl amino acid surfactants was determined on APHA scale by Lovibond PFX995/950. Fatty acid chlorides were analyzed as per the analytical method described in "Quantitative Organic Analysis Via Functional Groups", Editors: Sidney Siggia and J. Gordon Hanna, $4^{th}$ Edition (Pg. 223-230), John Wiley & Sons (1979).

Example 1

Preparation of Sodium Lauroyl Glycinate

It comprises of three steps a) Preparation of Catalyst I: N-lauroyl glycenic lauric anhydride (Formula IV, RCO=lauroyl, R=C11), b) Preparation of lauroyl chloride using Catalyst I and c) Preparation of sodium lauroyl glycinate: Schotten-Baumann reaction of lauroyl chloride with glycine in the presence of a base.

Preparation of Catalyst I: N-Lauroyl Glycenic Lauric Anhydride (Formula IV, RCO=Lauroyl, R=C11)

To a stirred mass of lauroyl chloride (6.0 g, 0.027 gmol) in dichloromethane (25 mL) under nitrogen blanket at 25° C., freshly oven dried sodium lauroyl glycinate (7.50 g, 0.027 gmol) was slowly added and the reaction mass was stirred for 12 hrs. The reaction mass was filtered and the solvent was removed under vacuum using a rotary evaporator to yield a white solid residue (9.4 g). It has a melting range of 125 to 130° C.

IR: 1643 $cm^{-1}$ of CO of amide, 3294 $cm^{-1}$ NH of amide, 1750 and 1817 $cm^{-1}$ CO of anhydride, 2849, 2917, 2954 $cm^{-1}$ CH stretching of alkyl chain NMR: ($CDCl_3$): δ0.86 to 0.89 (6H of two methyl groups of lauryl chains), 1.25 to 1.29 (34H, methylenes of alkyl chains), 1.63 to 1.67 (4H), 2.46 (2H). Melting range is 75-78° C.

Preparation of Lauroyl Chloride Using Catalyst I, N-Lauroyl Glycenic Lauric Anhydride (Formula IV, RCO=Lauroyl, R=C11):

To a stirred mass of lauric acid (200 g, 0.999 gmol) and N-lauroyl glycenic lauric anhydride (Formula IV, RCO=lauroyl, R=C11) from step I (0.6 g, 0.0013 gmol) at 25° C. under nitrogen blanket, thionyl chloride (123 g, 1.03 gmol) was added slowly at 25° C. and atmospheric pressure over a period of 2 hours maintaining temperature below 25° C. The hydrochloric acid and sulfur dioxide generated during the process was intermittently scrubbed in a gas scrubber containing caustic lye. The reaction mixture was stirred for additional 4 hours at the reaction temperature. The progress of reaction was monitored by measuring alkanoyl chloride formation and residual free fatty acid (Sidney Siggia and J. Gordon Hanna, "Quantitative Organic Analysis Via Functional Groups", $4^{th}$ Edition (Pg. 223-230), John Wiley & Sons (1979)). Nitrogen gas was purged through the reaction mass for 3 hours to remove the residual traces of sulfur dioxide, hydrogen chloride gas and unreacted thionyl chloride. At the end of this procedure lauroyl chloride (214 g, 98.0%) was obtained as practically colorless product. The detailed analysis is given in the Table 1.

TABLE 1

| Parameters | Analysis |
| --- | --- |
| Appearance | Clear liquid |
| Color (APHA scale) | 105 |
| % Purity | 97.40 |
| % Free fatty acid | 2.27 |

Preparation of Sodium Lauroyl Glycinate:
To a stirred solution of glycine (35 g, 0.47 gmol) in water (300 mL) at 10-15° C. under nitrogen blanket, lauroyl chloride (100 g, 0.45 gmol) and sodium hydroxide (36.5 g in 60 mL water ~40% solution, 0.91 gmol) were simultaneously added while maintaining the pH at 10.3 to 10.6 over 2 h. The reaction was continued for additional 3 hrs at 25 to 30° C. and maintaining the same pH range and finally the total weight was adjusted to 510 g by adding water to get the aqueous solution of sodium lauroyl glycinate with the following analysis as given in the Table 2.

TABLE 2

| Parameters | Analysis |
|---|---|
| Appearance | Clear liquid |
| Color (APHA scale) | 75 |
| % solids | 30.1 |
| % Sodium laurate | 1.5 |
| Viscosity | 1650 Cps |
| % Sodium chloride | 5.03 |

Example 2

Preparation of Sodium N-Lauroyl, N-Methyl Taurate

It comprises of three steps a) Preparation of Catalyst II: N-lauroyl, N-methyl taurinic lauric mix anhydride (Formula VI, RCO=lauroyl, R=C12), b) Preparation of lauroyl chloride using Catalyst II and c) Preparation of sodium N-lauroyl, N-methyl taurate: Schotten-Baumann reaction of lauroyl chloride with sodium N-methyl taurate in the presence of a base.

Preparation of Catalyst II: N-Lauroyl, N-Methyl Taurinic Lauric Mix Anhydride (Formula VI, RCO=Lauroyl, R=C11):

To a stirred mass of lauroyl chloride (6.0 g, 0.027 gmol) in dichoromethane (25 mL) under nitrogen blanket at 25° C., freshly oven dried sodium N-lauroyl, N-methyl taurate (9.28 g, 0.027 gmol) was slowly added and the reaction mass was stirred for 12 hrs. The reaction mass was filtered and the solvent was removed under vacuum using a rotary evaporator to yield a white solid residue (14 g).

IR: 1636 cm$^{-1}$ of CO of amide, 1723 and 1801 cm$^{-1}$ CO of anhydride, 2850, 2920, 2956 cm$^{-1}$ CH stretching of alkyl chain, 1173 and 1207 cm$^{-1}$ SO$_2$—O—.

Preparation of Lauroyl Chloride Using Catalyst II: N-Lauroyl, N-Methyl Taurinic Lauric Mix Anhydride (Formula VI, RCO=Lauroyl, R=C12):

To a stirred mass of lauric acid (200 g, 0.999 gmol) and N-lauroyl, N-methyl taurinic lauric mix anhydride (Formula V, RCO=lauroyl, C12) from step I (0.6 g, 0.0012 gmol) at 25° C. under nitrogen blanket, thionyl chloride (123 g, 1.03 gmol) was added slowly at 25° C. and atmospheric pressure over a period of 2 hours maintaining temperature below 25° C. The hydrochloric acid and sulfur dioxide generated during the process was continuously scrubbed in a gas scrubber containing caustic lye. The reaction mixture was stirred for additional 4 hours at the reaction temperature. The progress of reaction in the last phase was monitored by measuring alkanoyl chloride formation. Nitrogen gas was purged through the reaction mass for 3 hours to remove the residual traces of sulfur dioxide, hydrogen chloride gas and unreacted thionyl chloride. At the end of this procedure lauroyl chloride (212 g, 97%) was obtained as practically colorless product.

The detailed analysis is given in the Table 3.

TABLE 3

| Parameters | Analysis |
|---|---|
| Appearance | Clear liquid |
| Color (APHA scale) | 85 |
| % Purity | 98.00 |
| % Free fatty acid | 1.57 |

Preparation of Sodium N-Lauroyl, N-Methyl Taurate:

To a stirred solution of sodium N-methyl taurate (74 g, 0.46 mmol) in water (450 mL) at 10-15° C. under nitrogen blanket, lauroyl chloride (100 g, 0.45 gmol) and sodium hydroxide (18 g in 30 mL water, ~40% solution, 0.45 gmol) were simultaneously added while maintaining the pH at 10.3 to 10.6 over 4 h. The reaction was continued for additional 3 hrs at 25 to 30° C. and maintaining the same pH. Finally the total weight was adjusted to 640 g to yield aqueous solution of sodium N-lauroyl, N-methyl taurate with the following analysis as given in the Table 4.

TABLE 4

| Parameters | Analysis |
|---|---|
| Appearance | Clear liquid |
| Color (APHA scale) | 125 |
| % solids | 30.11 |
| % Sodium cocoate | 1.5 |
| Viscosity | 150 Cps |
| % Sodium chloride | 4.1 |

Example 3

Preparation of Sodium Cocoyl Glycinate

It comprises of three steps a) Preparation of Catalyst I: N-cocoyl glycenic cocoyic anhydride (Formula IV, RCO=cocoyl, R=C6 to C18) b) Preparation of cocoyl chloride using Catalyst I and c) Preparation of sodium cocoyl glycinate: Schotten-Baumann reaction of cocoyl chloride with glycine in the presence of a base.

Coco fatty acid that was used to make the catalyst I (N-cocoyl glycenic cocoyic anhydride (Formula IV, RCO=cocoyl, R=C6 to C18), as well as to make cocoyl chloride had the following composition:

$C_8$ (Caprylic acid)—5.38%
$C_{10}$ (Capric acid)—5.78%
C12 (Lauric acid)—61.37%
$C_{14}$ (Myristic acid—20.77%
$C_{16}$ (Palmitic acid)—4.7% and
$C_{18}$ (Stearic acid)—2.0%

Preparation of Catalyst I: N-Cocoyl Glycenic Cocoic Anhydride (Formula IV, RCO=Cocoyl, C8 to C18):

To a stirred mass of cocoyl chloride (10 g, 0.045 gmol) in dichloromethane (50 mL) under nitrogen blanket at 25° C., freshly oven dried sodium cocoyl glycinate (12.5 g, 0.045 gmol) was slowly added and the reaction mass was stirred for 12 hrs. The reaction mass was filtered and the solvent was removed under vacuum using a rotary evaporator to yield the anhydride as a white solid residue (20 g).

IR: 1645 cm$^{-1}$ of CO of amide, 3206 cm$^{-1}$ NH of amide, 1750 and 1816 cm$^{-1}$ CO of anhydride, 2849, 2917, 2954 cm$^{-1}$ CH stretching of alkyl chain.

Preparation of Cocoyl Chloride Using Catalyst I, N-Cocoyl Glycenic Cocoyic Anhydride (Formula IV, RCO=Cocoyl, R=C6 to C18):

To a stirred mass of coco fatty acid (200 g, 0.99 gmol) and N-cocoyl glycenic cocoyic anhydride (Formula IV, RCO=cocoyl, R=C6 to C18) from step I (0.6 g, 0.0013 gmol) at 25° C. under nitrogen blanket, thionyl chloride (123 g, 1.03 gmol) was added slowly at 25° C. and atmospheric pressure over a period of 2 hours maintaining temperature below 25° C. The hydrochloric acid and sulfur dioxide generated during the process was continuously scrubbed in a gas scrubber containing caustic lye. The reaction mixture was stirred for additional 4 hours at the reaction temperature. The progress of reaction was monitored by measuring alkanoyl chloride formation. Nitrogen gas was purged through the reaction mass for 3 hours to remove the residual traces of sulfur dioxide, hydrogen chloride gas and unreacted thionyl chloride. At the end of this procedure cocoyl chloride (212 g, 97%) was obtained as practically colorless product. The detailed analysis is given in the Table 5.

TABLE 5

| Parameters | Analysis |
|---|---|
| Appearance | Clear liquid |
| Color (APHA scale) | 85 |
| % Purity | 98.6 |
| % Free fatty acid | 1.35 |

Preparation of Sodium Cocoyl Glycinate:

To a stirred solution of glycine (35.0 g, 0.47 gmol) in water (300 mL) at 10-15° C. under nitrogen blanket, cocoyl chloride (100 g, 0.45 gmol) and sodium hydroxide (36.5 g in 60 mL, ~40% solution, 0.91 gmol) were simultaneously added while maintaining the pH at 10.3 to 10.6 over 4 h. The reaction was continued for additional 3 hrs and maintaining the same pH range and the final weight was adjusted to 510 g to yield aqueous solution of sodium cocoyl glycinate with the following analysis as given in the Table 6.

TABLE 6

| Parameters | Analysis |
|---|---|
| Appearance | Clear liquid |
| Color (APHA scale) | 125 |
| % solids | 29.98 |
| % Sodium cocoate | 1.67 |
| Viscosity | 1200 Cps |
| % Sodium chloride | 4.93 |

Example 4

Preparation of Sodium Cocoyl Glycinate: Two Step Procedure: In-Situ Catalyst Generation Preparation of sodium cocoyl glycinate by a two step procedure that comprises of a) Preparation of cocoyl chloride from coco fatty acid and thionyl chloride in the presence of catalytic amount of a sodium cocoyl glycinate and b) Preparation of sodium cocoyl glycinate from cocoyl chloride of step (a) and glycine in aqueous medium.

Preparation of Cocoyl Chloride from Coco Fatty Acid and Thionyl Chloride in the Presence of Catalytic Amount of a Sodium Cocoyl Glycinate:

Coco fatty acid that was used to make the catalyst I (N-cocoyl glycenic cocoyic anhydride (Formula IV, RCO=cocoyl, C6 to C18), as well as to make cocoyl chloride had the following composition:

$C_8$ (Caprylic acid)—5.38%
$C_{10}$ (Capric acid)—5.78%
$C_{12}$ (Lauric acid)—61.37%
$C_{14}$ (Myristic acid—20.77%
C16 (Palmitic acid)—4.7% and
$C_{18}$ (Stearic acid)—2.0%

Preparation of Cocoyl Chloride by In-Situ Generation of Catalyst I, N-Cocoyl Glycenic Cocoyic Anhydride (Formula IV, RCO=Cocoyl, R=C6 to C18):

To a stirred mass of coco fatty acid (200 g, 0.99 gmol) and sodium cocoyl glycinate (0.6 g, 0.002 gmol) at 25° C. under nitrogen blanket, thionyl chloride (123 g, 1.03 gmol) was added slowly at 25° C. and atmospheric pressure over a period of 2 hours maintaining temperature below 25° C. The hydrochloric acid and sulfur dioxide generated during the process was continuously scrubbed in a gas scrubber containing caustic lye. The reaction mixture was stirred for additional 4 hours at the reaction temperature. The progress of reaction was monitored by measuring alkanoyl chloride formation. Nitrogen gas was purged through the reaction mass for 3 hours to remove the residual traces of sulfur dioxide, hydrogen chloride gas and unreacted thionyl chloride. At the end of this procedure cocoyl chloride (218 g, 98.8%) was obtained as practically colorless product. The detailed analysis is given in the Table 7.

TABLE 7

| Parameters | Analysis |
|---|---|
| Appearance | Clear liquid |
| Color (APHA scale) | 92 |
| % Purity | 98.45 |
| % Free fatty acid | 1.2 |

Preparation of Sodium Cocoyl Glycinate from Cocoyl Chloride from Step (a) and Glycine in Aqueous Medium:

Preparation of Sodium Cocoyl Glycinate:

To a stirred solution of glycine (35 g, 0.47 gmol) in water (300 mL) at 10-15° C. under nitrogen blanket, cocoyl chloride (100 g, 0.45 gmol) and sodium hydroxide (36.5 g in 60 mL water, ~40% solution, 0.91 gmol) were simultaneously added while maintaining the pH at 10.3 to 10.6 over 4 h. The reaction was continued for additional 3 hrs and maintaining the same pH range. Finally the weight was adjusted to yield (510 g) aqueous solution of sodium cocoyl glycinate with the following analysis as given in the Table 8.

TABLE 8

| Parameters | Analysis |
|---|---|
| Appearance | Clear liquid |
| Color (APHA scale) | 112 |
| % solids | 30 |
| % Sodium cocoate | 1.78 |
| Viscosity | 1250 Cps |
| % Sodium chloride | 5.2 |

Example 5

Preparation of Sodium Lauroyl Sarcosinate

It comprises of two steps a) Preparation of lauroyl chloride using sodium lauroyl sarcosinate and b) Preparation of sodium lauroyl sarcosinate: Schotten-Baumann reaction of lauroyl chloride with sodium sarcosinate in the presence of a base.

Preparation of Lauroyl Chloride Using Sodium Lauroyl Sarcosinate as Catalyst:

To a stirred mass of lauric acid (200 g, 1.0 gmol) and sodium N-lauroyl sarcosinate (0.6 g, 0.002 gmol) at 25° C. under nitrogen blanket, thionyl chloride (123 g, 1.03 gmol) was added slowly at 25° C. and atmospheric pressure over a period of 2 hours maintaining temperature below 25° C. The hydrochloric acid and sulfur dioxide generated during the process was scrubbed in a gas scrubber containing caustic lye. The reaction mixture was stirred for additional 4 hours at the reaction temperature. The progress of reaction was monitored by measuring alkanoyl chloride formation after completion of addition.

Nitrogen gas was purged through the reaction mass for 3 hours to remove the residual traces of sulfur dioxide, hydrogen chloride gas and unreacted thionyl chloride. At the end of this procedure lauroyl chloride (213 g, 97.5%) was obtained as practically colorless product. The detailed analysis is given in the Table 9.

TABLE 9

| Parameters | Analysis |
| --- | --- |
| Appearance | Clear liquid |
| Color (APHA scale) | 150 |
| % Purity | 97.40 |
| % Free fatty acid | 2.27 |

Preparation of Sodium Lauroyl Sarcosinate:

To a stirred solution of sodium sarcosinate (52 g, 0.47 mmol) in water (330 mL) at 10-15° C. under nitrogen blanket, lauroyl chloride (100 g, 0.45 mmol) and sodium hydroxide (18.0 g in 60 mL water ~40% solution, 0.455 mmol) were simultaneously added while maintaining the pH at 10.3 to 10.6 over 2 h. The reaction was continued for additional 3 hrs at 25 to 30° C. and maintaining the same pH range and the final weight was adjusted to yield (540 g) aqueous solution of sodium lauroyl sarcosinate with the following analysis as given in the Table 10.

TABLE 10

| Parameters | Analysis |
| --- | --- |
| Appearance | Clear liquid |
| Color (APHA scale) | 125 |
| % solids | 30.3 |
| % Sodium laurate | 1.76 |
| Viscosity | 700 Cps |
| % Sodium chloride | 4.72 |

Example 6

Preparation of Sodium Lauroyl Glycinate: Two Step Procedure: In-Situ Catalyst Generation Preparation of sodium lauroyl glycinate by a two step procedure that comprises of a) Preparation of lauroyl chloride from lauric acid and thionyl chloride in the presence of catalytic amount of a sodium lauroyl glycinate and b) Preparation of sodium lauroyl glycinate from lauroyl chloride of step (a) and glycine in aqueous medium.
Preparation of Lauroyl Chloride by In-Situ Generation of Catalyst I, N-Lauroyl Glycenic Lauric Anhydride (Formula IV, RCO=Lauroyl R=C 11):

To a stirred mass of lauric acid (200 g, 1.0 gmol) and sodium lauroyl glycinate (0.6 g, 0.002 gmol) at 25° C. under nitrogen blanket, thionyl chloride (123 g, 1.03 gmol) was added slowly at 25° C. and atmospheric pressure over a period of 2 hours maintaining temperature below 25° C. The hydrochloric acid and sulfur dioxide generated during the process was continuously scrubbed in a gas scrubber containing caustic lye. The reaction mixture was stirred for additional 4 hours at the reaction temperature. The progress of reaction was monitored by measuring alkoyl chloride formation. Nitrogen gas was purged through the reaction mass for 3 hours to remove the residual traces of sulfur dioxide, hydrogen chloride gas and unreacted thionyl chloride. At the end of this procedure lauroyl chloride (218 g, 99.8%) was obtained as practically colorless product. The detailed analysis is given in the Table 11.

TABLE 11

| Parameters | Analysis |
| --- | --- |
| Appearance | Clear liquid |
| Color (APHA scale) | 85 |
| % Purity | 98.5 |
| % Free fatty acid | 1.56 |

Preparation of Sodium Lauroyl Glycinate from Lauroyl Chloride from Step (a) and Glycine in Aqueous Medium:
Preparation of Sodium lauroyl Glycinate:

To a stirred solution of glycine (35 g, 0.47 gmol) in water (300 mL) at 10-15° C. under nitrogen blanket, lauroyl chloride (100 g, 0.457 gmol) and sodium hydroxide (36.5 g in 60 mL water, ~40% solution, 0.91 gmol) were simultaneously added while maintaining the pH at 10.3 to 10.6 over 4 h. The reaction was allowed to come to room temp and continued for additional 3 hrs at 25-30° C. and maintaining the same pH range and finally the weight was adjusted to yield (520 g) aqueous solution of sodium lauroyl glycinate with the following analysis as given in the Table 12.

TABLE 12

| Parameters | Analysis |
| --- | --- |
| Appearance | Clear liquid |
| Color (APHA scale) | 125 |
| % solids | 30 |
| % Sodium laurate | 1.5 |
| Viscosity | 1600 Cps |
| % Sodium chloride | 4.9 |

Example 7

Preparation of Sodium N-Lauroyl, N-Methyl Taurate: Two Step Procedure: In-Situ Catalyst Generation Preparation of sodium N-lauroyl, N-methyl taurate by a two step procedure that comprises of a) Preparation of lauroyl chloride from lauric acid and thionyl chloride in the presence of sodium N-lauroyl, N-methyl taurate and b) Schotten-Baumann reaction of lauroyl chloride of step (a) with sodium N-methyl taurate in the presence of a base.
Preparation of Lauroyl Chloride by In-Situ Generation of Catalyst II, N-Lauroyl, N-Methyl Taurinic Lauric Mix Anhydride (Formula VI, RCO=Lauroyl, R=C11):

To a stirred mass of lauric acid (200 g, 0.999 gmol) and sodium N-lauroyl, N-methyl taurate (0.6 g, 0.0017 gmol) at 25° C. under nitrogen blanket, thionyl chloride (123 g, 1.03 gmol) was added slowly at 25° C. and atmospheric pressure over a period of 2 hours maintaining temperature below 25° C. The hydrochloric acid and sulfur dioxide generated during the process was continuously scrubbed in a gas scrubber containing caustic lye. The reaction mixture was stirred for additional 4 hours at the reaction temperature. The progress of reaction in the last phase was monitored by measuring alkanoyl chloride formation. Nitrogen gas was purged through the reaction mass for 3 hours to remove the residual traces of sulfur dioxide, hydrogen chloride gas and unreacted thionyl chloride. At the end of this procedure lauroyl chloride (212 g, 97%) was obtained as practically colorless product. The detailed analysis is given in the Table 13.

TABLE 13

| Parameters | Analysis |
| --- | --- |
| Appearance | Clear liquid |
| Color (APHA scale) | 85 |
| % Purity | 98.00 |
| % Free fatty acid | 1.57 |

Preparation of Sodium N-Lauroyl, N-Methyl Taurate:

To a stirred solution of sodium N-methyl taurate (74 g, 0.46 gmol) in water (400 mL) at 10-15° C. under nitrogen blanket, lauroyl chloride (100 g, 0.45 gmol) and sodium hydroxide (18 g in 30 mL water, ~40% solution, 0.45 gmol) were simultaneously added while maintaining the pH at 10.3 to 10.6 over 4 h. The reaction was allowed to come to room continued for additional 3 hrs at 25 to 30° C. and maintaining the pH and finally the weight was adjusted to yield 602 g of aqueous solution of sodium N-lauroyl, N-methyl taurate with the following analysis as given in the Table 14.

TABLE 14

| Parameters | Analysis |
| --- | --- |
| Appearance | Clear liquid |
| Color (APHA scale) | 125 |
| % solids | 30 |
| % Sodium laurate | 1.5 |
| Viscosity | 100 Cps |
| % Sodium chloride | 4.2 |

Example 8

Preparation of Sodium Cocoyl Glycinate: Two Step Procedure: In-Situ Catalyst Generation Preparation of sodium cocoyl glycinate by a two step procedure that comprises of a) Preparation of cocoyl chloride from coco fatty acid and thionyl chloride in the presence of catalytic amount of a sodium N-cocoyl, N-methyl taurate and b) Preparation of sodium cocoyl glycinate from cocoyl chloride of step (a) and glycine in aqueous medium.
Preparation of Cocoyl Chloride from Coco Fatty Acid and Thionyl Chloride in the Presence of Catalytic Amount of Sodium N-Cocoyl, N-Methyl Taurate:

Coco fatty acid that was used to make cocoyl chloride had the following composition:
$C_8$ (Caprylic acid)—5.38%
$C_{10}$ (Capric acid)—5.78%
$C_{12}$ (Lauric acid)—61.37%
$C_{14}$ (Myristic acid—20.77%
$C_{16}$ (Palmitic acid)—4.7% and
$C_{18}$ (Stearic acid)—2.0%

Preparation of Cocoyl Chloride by In-Situ Generation of Catalyst II, N-Cocoyl Taurinic Cocoyic Anhydride (Formula VI, RCO=Cocoyl, R=C6 to C18, $R_2$=Methyl)

To a stirred mass of coco fatty acid (200 g, 1.0 gmol) and sodium N-cocoyl, N-methyl taurate (0.6 g, 0.0017 gmol) at 25° C. under nitrogen blanket, thionyl chloride (123 g, 1.029 gmol) was added slowly at 25° C. and atmospheric pressure over a period of 2 hours maintaining temperature below 25° C. The hydrochloric acid and sulfur dioxide generated during the process was continuously scrubbed in a gas scrubber containing caustic lye. The reaction mixture was stirred for additional 4 hours at the reaction temperature. The progress of reaction was monitored by measuring alkanoyl chloride formation. Nitrogen gas was purged through the reaction mass for 3 hours to remove the residual traces of sulfur dioxide, hydrogen chloride gas and unreacted thionyl chloride. At the end of this procedure cocoyl chloride (218 g, 100%) was obtained as practically colorless product. The detailed analysis is given in the Table 15.

TABLE 15

| Parameters | Analysis |
| --- | --- |
| Appearance | Clear liquid |
| Color (APHA scale) | 78 |
| % Purity | 98.56 |
| % Free fatty acid | 1.00 |

Preparation of Sodium Cocoyl Glycinate from Cocoyl Chloride from Step (a) and Glycine in Aqueous Medium.
Preparation of Sodium Cocoyl Glycinate:

To a stirred solution of glycine (35 g, 0.47 gmol) in water (300 mL) at 10-15° C. under nitrogen blanket, cocoyl chloride (100 g, 0.45 gmol) and sodium hydroxide (36.5 g in 60 mL water, ~40% solution, 0.91 gmol) were simultaneously added while maintaining the pH at 10.3 to 10.6 over 4 h. The reaction was continued for additional 3 hrs and maintaining the same pH range. Finally the weight was adjusted to yield (520 g) aqueous solution of sodium cocoyl glycinate with the following analysis as given in the Table 16.

TABLE 16

| Parameters | Analysis |
| --- | --- |
| Appearance | Clear liquid |
| Color (APHA scale) | 112 |
| % solids | 30.1 |
| % Sodium cocoate | 1.58 |
| Viscosity | 1330 Cps |
| % Sodium chloride | 5.12 |

The invention claimed is:
1. A process of producing N-acyl amino acid based surfactants of Formula I,

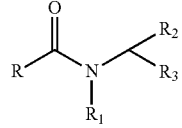

Formula I wherein, R is selected from C6 to C22 alkyl group, $R_1$ is selected from H, C1 to C4 alkyl, $R_2$ is selected from all groups on α carbon of natural amino acids, $R_3$ is selected from COOX, $CH_2$—$SO_3X$, X is selected from $Li^+$, $Na^+$ or $K^+$;

said process comprising steps of

A) preparing fatty acid chlorides by halogenating fatty acids with thionyl chloride in the presence of catalytic amount of same or other N-acyl amino acid surfactant of Formula I or anhydrides of same surfactant, Formula II,

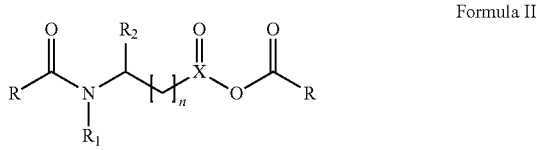

Formula II wherein, R=C6 to C22 alkyl group, $R_1$=H, C1 to C4 alkyl, $R_2$=all groups on α carbon of natural amino acids, n=0 to 4, X=C, SO and B) reacting fatty acid chloride of step (A) with an amino acid in the presence of a base under typical aqueous Schotten Baumann conditions.

2. The process as claimed in claim 1, wherein the catalytic amount of compounds of Formula I and Formula II, is 0.05 to 0.5% by weight based on fatty acid.

3. The process as claimed in claim 1, wherein the amino acids used in the synthesis of compounds of Formula I are selected from naturally occurring α-amino acids.

4. The process as claimed in claim 1, wherein the naturally occurring α-amino acids are selected from Glycine, Alanine, Valine, Leucine, Isoleucine, Methionine, Proline, Cystein, Phenyl alanine, Tyrosine, Tryptophan, Arginine, Lysine, Histidine, Aspartic acid, Glutamic acid, Serine, Threonine, Aspergine and Glutamine.

5. The process as claimed in claim 1, wherein the amino acids used in the synthesis of compounds of Formula I are selected from unnatural amino acids and mixtures of stereoisomers.

6. The process as claimed in claim 1, wherein the unnatural amino acids are selected from amino propionic acid, N-methyl taurine and Sarcosine.

7. The process as claimed in claim 1, wherein halogenations of fatty acids with thionyl chloride are carried out at 20 to 45° C.

8. The process as claimed in claim 3, wherein the naturally occurring α-amino acids are selected from Glycine, Alanine, Valine, Leucine, Isoleucine, Methionine, Proline, Cystein, Phenyl alanine, Tyrosine, Tryptophan, Arginine, Lysine, Histidine, Aspartic acid, Glutamic acid, Serine, Threonine, Aspergine and Glutamine.

9. The process as claimed in claim 5, wherein the unnatural amino acids are selected from amino propionic acid, N-methyl taurine and Sarcosine.

\* \* \* \* \*